US007925346B1

(12) United States Patent
Go

(10) Patent No.: US 7,925,346 B1
(45) Date of Patent: Apr. 12, 2011

(54) MODEL FOR PREDICTION OF PACED ATRIAL ACTIVATION TIME AND INTERATRIAL CONDUCTION DELAY

(75) Inventor: Andre Go, Raleigh, NC (US)

(73) Assignee: Pacesetter, Inc., Sylmar, CA (US)

( * ) Notice: Subject to any disclaimer, the term of this patent is extended or adjusted under 35 U.S.C. 154(b) by 446 days.

(21) Appl. No.: 11/623,389

(22) Filed: Jan. 16, 2007

(51) Int. Cl.
*A61N 1/362* (2006.01)
(52) U.S. Cl. .......................................................... 607/9
(58) Field of Classification Search .......... 607/9; 703/6, 703/11
See application file for complete search history.

(56) References Cited

U.S. PATENT DOCUMENTS

| 4,108,148 | A | 8/1978 | Cannon, III |
| 5,179,949 | A | 1/1993 | Chirife |
| 5,507,782 | A | 4/1996 | Kieval et al. |
| 6,314,323 | B1 | 11/2001 | Ekwall |
| 6,650,931 | B1 | 11/2003 | McClure et al. |
| 6,748,261 | B1 * | 6/2004 | Kroll et al. ................ 600/510 |
| 7,248,925 | B2 | 7/2007 | Bruhns et al. |
| 7,310,554 | B2 * | 12/2007 | Kramer et al. ................ 607/9 |
| 2002/0151934 | A1 | 10/2002 | Levine |
| 2002/0151935 | A1 | 10/2002 | Levine |
| 2003/0014084 | A1 | 1/2003 | VanHout |
| 2003/0032991 | A1 | 2/2003 | Poore |
| 2003/0060850 | A1 * | 3/2003 | Zhu et al. ................ 607/9 |
| 2003/0083700 | A1 | 5/2003 | Hill |
| 2004/0147966 | A1 | 7/2004 | Ding et al. |
| 2005/0137630 | A1 | 6/2005 | Ding et al. |
| 2005/0137632 | A1 * | 6/2005 | Ding et al. ................ 607/9 |
| 2008/0140147 | A1 * | 6/2008 | Husby ................ 607/30 |

FOREIGN PATENT DOCUMENTS

EP 0494387 B1 1/1996

OTHER PUBLICATIONS

Chirife et al. Automatic Beat-to-Beat Left Heart AV Normalization: Is It Possible? Pacing and Clinical Electrophysiology. (2003) 26:11; p. 2103-2110.*
Chirife, Raul et al., "Automatic Beat-to-Beat Left Heart AV Normalization: Is it Possible?" PACE. 2003;26:2103-2110.
Koglek, W. et al., "A simple method for AV-delay determiantion in dual chamber pacemakers," Herzschrittmacher. Elektrophysiol. 2000;11(4):244-253 (pp. 1-16 provided in English).
Strohmer, Bernhard et al., "Evaluation of Atrial Conduction Time at Various Sites of Right Atrial Pacing and Influence on Atrioventricular Delay Optimization by Surface Electrocardiography," PACE. 2004;27:468-474.

(Continued)

*Primary Examiner* — Carl H Layno
*Assistant Examiner* — Jeremiah T Kimball

(57) ABSTRACT

An exemplary device includes control logic to determine a paced atrial activation time using a predictive model and an intrinsic atrial activation time and to determine an atrioventricular delay based at least in part on the paced atrial activation time. Such a device may be an implantable device configured to deliver cardiac therapy that uses atrial pacing and ventricular pacing. Such a device may be a programmer configured to program an implantable device configured to deliver cardiac therapy that uses atrial pacing and ventricular pacing. Various other exemplary technologies are also disclosed.

22 Claims, 9 Drawing Sheets

OTHER PUBLICATIONS

Strohmer, B. et al., "Validation of Total Atrial Conduction Time by Surface-ECG at Various Right Atrial Pacing Sites," Europace. 2003.

Strohmer, B. et al., "AV-Delay Optimization Guided by Surface ECG: Impact on Stroke volume in DDD Pacing," Europace. 2003.

Levine, P. MD FACC, "Programming the AV Delay," Supplement A—Guidelines to the Routing Evaluation, Programming and Follow-up of the Patient with an Implanted Dual-Chamber Modulated Pacing System. 2003:119-128.

Yu, Y. et al., "Optimziation of AV Delay in DDD Mode of Cardiac Resynchronization Therapy for Heart Failure Patients," Europace Supplements. Dec. 2003, vol. 4-Abstract A30-6.

NonFinal Office Action, mailed Aug. 15, 2006: Related U.S. Appl. No. 10/928,586.

Notice of Allowance, mailed Mar. 23, 2007: Related U.S. Appl. No. 10/928,586.

* cited by examiner

EXEMPLARY DATA AND METHOD 400

MODEL FOR PREDICTION OF PACED ATRIAL ACTIVATION TIME AND INTERATRIAL CONDUCTION DELAY

RELATED APPLICATIONS

This application is related to co-pending U.S. patent application Ser. No. 10/928,586, filed on Aug. 27, 2004, SYSTEM AND METHOD FOR DETERMINING OPTIMAL ATRIOVENTRICULAR DELAY BASED ON INTRINSIC CONDUCTION DELAYS, the specification thereof is incorporated herein by reference.

TECHNICAL FIELD

Exemplary technologies presented herein generally relate to cardiac pacing and/or stimulation therapy. Various techniques provide for prediction of interatrial conduction delays.

BACKGROUND

The sinus node is known as the heart's natural "pacemaker". The sinoatrial node is a group of cells positioned on the wall of the right atrium, near the entrance of the superior vena cava. Impulses originating at the sinoatrial node conduct via myocardial tissue toward the atrial septum and hence toward the left atrium. At the atrial septum, conduction to the ventricles occurs via the atrioventricular node. As the sinoatrial node is located in the right atrium, right atrial contraction occurs prior to left atrial contraction. The right atrium fills the right ventricle and the left atrium fills the left ventricle, which is the main driver for blood circulation through the body. Thus, timing of the left atrial contraction impacts diastolic and systolic function of the left ventricle and hence the left ventricle's ejection volume, efficiency and overall ability to provide blood to the body. Consequently, left ventricular hemodynamics are critical to avert patient symptoms and increase exercise capacity in the heart failure population.

To understand better the relationship between sinoatrial node activity and contraction of the left atrium, an interatrial conduction delay is defined as the time difference between a right atrial event (e.g., an intrinsic event, a paced event, a characteristic of a right atrial electrical activity waveform, etc.) and a left atrial event (e.g., a characteristic of a left atrial electrical activity waveform, etc.). As described herein, various exemplary techniques allow for predicting (or estimating) interatrial conduction delay for paced atrial events. Such techniques are beneficial for clinician guidance and for programming paced and sensed atrioventricular delays. Such techniques may be in the form of a validated model, optionally coded into an implantable device and/or other computing device (e.g., device programmer) via software and/or hardware. Thus, such techniques may be used to suggest or set appropriate AV delays either automatically or on demand. Other exemplary techniques are also disclosed.

SUMMARY

An exemplary device includes control logic to determine a paced atrial activation time using a predictive model and an intrinsic atrial activation time and to determine an atrioventricular delay based at least in part on the paced atrial activation time. Such a device may be an implantable device configured to deliver cardiac therapy that uses atrial pacing and ventricular pacing. Such a device may be a programmer configured to program an implantable device configured to deliver cardiac therapy that uses atrial pacing and ventricular pacing. Various other exemplary technologies are also disclosed. In general, the various methods, devices, systems, etc., described herein, and equivalents thereof, are suitable for use in a variety of pacing therapies and/or other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators are used at times to reference like parts or elements throughout the description.

Overview

Exemplary techniques pertain generally to interatrial conduction delay and more specifically to relationships between intrinsic interatrial conduction delays and paced interatrial conduction delays. For example, various exemplary methods include using a model to predict a paced interatrial conduction delay (or paced atrial activation time) given an intrinsic interatrial conduction delay (or intrinsic atrial activation time). A particular model uses a linear equation with parameters fitted by applying a regression analysis to data for a group of patients. Such prediction or estimation techniques may be used for any of a variety of purposes including determination of atrioventricular pacing delay and determination of left ventricular pacing time to avoid premature left ventricular contraction (i.e., to allow for adequate left ventricular filling).

While a model based on data from a group of patients is presented, a model may be based on data from a single patient. Further, a model may account for rate information and thereby allow for prediction of an interatrial conduction delay based at least in part on atrial rate, whether intrinsic or paced.

The following description begins with a discussion of exemplary implantable devices and associated components followed by a discussion of an exemplary linear model for paced atrial activation time versus intrinsic atrial activation time and an exemplary linear model of difference between paced atrial activation time and intrinsic atrial activation time versus intrinsic atrial activation time. Next, a discussion of various exemplary methods for using such models follows, and the detailed description continues with a discussion of an exemplary system that may be used to acquire data, generate or fit models and/or to implement various exemplary methods.

Exemplary Stimulation Device

The techniques described below are intended to be implemented in connection with any stimulation device that is configured or configurable to stimulate nerves and/or stimulate and/or shock a patient's heart.

Figure 1:
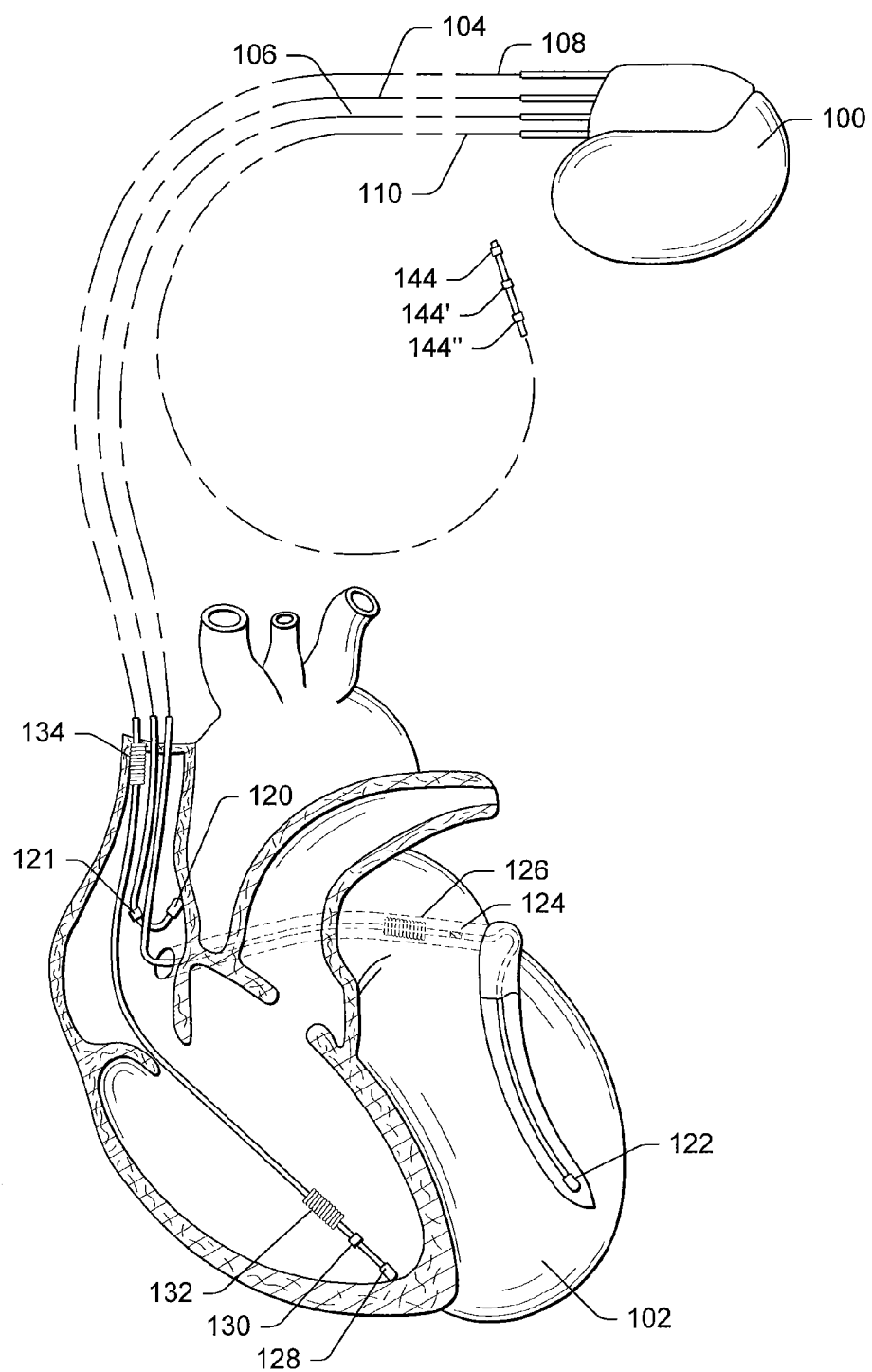
FIG. 1 is a simplified diagram illustrating an exemplary implantable stimulation device in electrical communication with at least three leads implanted into a patient's heart and at least one other lead for sensing, delivering stimulation and/or delivering shock therapy. Other devices with fewer leads may also be suitable.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves or other nerves. In addition, the device 100 includes a fourth lead 110 having, in this implementation, three electrodes 144, 144', 144" suitable for stimulation of autonomic nerves or other nerves. This lead may be positioned in and/or near a patient's heart or near an autonomic nerve within a patient's body and remote from the heart. Of course, such a lead may be positioned epicardially or at some other location to stimulate other tissue.

The right atrial lead 104, as the name implies, is positioned in and/or passes through a patient's right atrium. The right atrial lead 104 can be used to sense atrial electrical activity (e.g., cardiac signals) and/or to provide right atrial chamber stimulation and/or stimulation therapy. As shown in FIG. 1, the stimulation device 100 is coupled to the implantable right atrial lead 104, which includes an atrial tip electrode 120. In various patient trials discussed below, an atrial tip electrode was implanted in the right atrial appendage of each patient. The lead 104, as shown in FIG. 1, also includes an atrial ring electrode 121. Of course, the lead 104 may have other electrodes as well. For example, the right atrial lead optionally includes a distal bifurcation having electrodes suitable for stimulation and/or sensing.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference.

The coronary sinus lead 106 further optionally includes electrodes for stimulation of autonomic nerves or other nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

As described in more detail below, a coronary sinus lead may include a series of electrodes for acquiring left atrial electrical activity. Such information may be used for generating or fitting a model (see, e.g., the lead 301 of FIG. 3).

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve or other nerve, such an electrode may be positioned on the lead or a bifurcation or leg of the lead.

Figure 2:
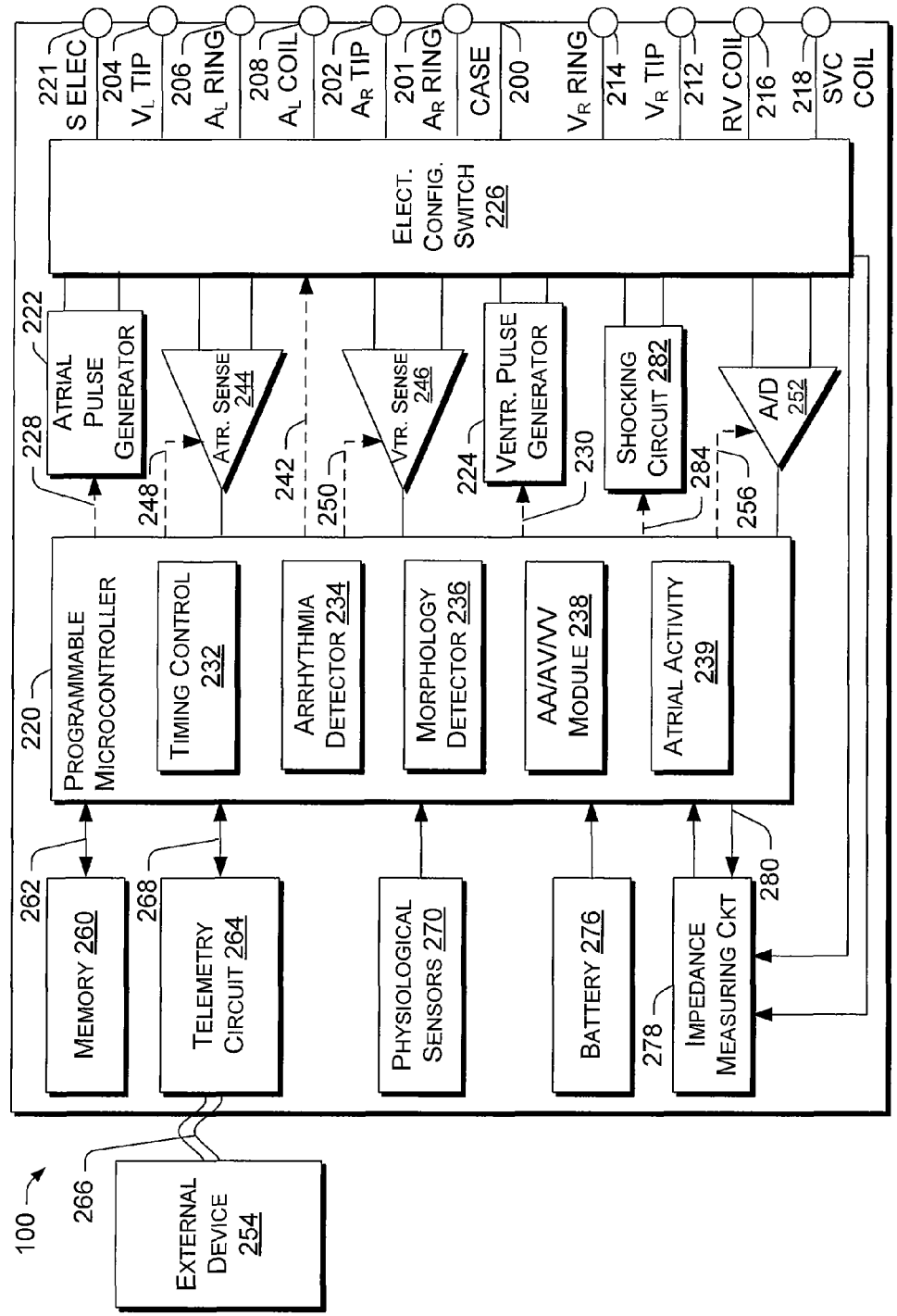
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense or otherwise acquire information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves or other nerves. While a particular multi-chamber device is shown, it is to be appreciated and understood that this is done for illustration purposes only. For example, various methods may be implemented on a pacing device suited for single ventricular stimulation and not bi-ventricular stimulation. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or nerve stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or nerve stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable nerve stimulation electrodes is also possible via these and/or other terminals (e.g., via a nerve stimulation terminal S ELEC 221).

To support right chamber sensing, pacing, shocking, and/or nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code (e.g., control logic) stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. Pulses may also be directed to the connector S ELEC 221, for example, to deliver energy via the lead 110. It is understood that in order to provide stimulation therapy in each of the four chambers of the heart (or to nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrioventricular (e.g., AV) delay, interatrial conduction (AA) delay, or interventricular conduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an AA delay, AV delay and/or VV delay module 238 for performing a variety of tasks related to AA delay, AV delay and/or VV delay. This component can be utilized by the stimulation device 100 for determining desirable times to administer various therapies, including, but not limited to, ventricular stimulation therapy, bi-ventricular stimulation therapy, resynchronization therapy, atrial stimulation therapy, etc. The AA/AV/VV module 238 may be implemented in hardware as part of the microcontroller 220, or as software/firmware instructions programmed into the device and executed on the microcontroller 220 during certain modes of operation. Of course, such a module may be limited to one or more of the particular functions of AA delay, AV delay and/or VV delay. Such a module may include other capabilities related to other functions that may be germane to the delays.

The microcontroller 220 of FIG. 2 also includes an atrial activity module 239. This module may include control logic for one or more atrial activity related features. For example, the module 239 may include an algorithm for determining paced interatrial conduction delay based on an intrinsic interatrial conduction delay. The module 239 may further perform actions to acquire data for use in generating a model and/or fitting a model and the module 239 may include instructions for generating a model and/or fitting a model. For example, the module 239 may acquire data and then perform a regression using one or more models to thereby fit the data to the one or more models. In turn, the model or models may be used to determine parameters for use in a pacing therapy, assessment of patient condition, etc. The module 239 may include instruction for updating or otherwise adjusting a model, as appropriate (e.g., using a schedule, responsive to an event notification, responsive to a clinician instruction, etc.).

Various algorithms are described in more detail with respect to the figures. The module 239 may be implemented in hardware as part of the microcontroller 220, or as software/firmware instructions programmed into the device and executed on the microcontroller 220 during certain modes of operation. The module 239 may act cooperatively with the AA/AV/VV module 238.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art. The switch 226 may also select an electrode or electrodes of an electrode configuration for use in sensing cardiac electrical activity. For example, as already mentioned, the lead 106 may include a series of electrodes, optionally defined in pairs. In this example, the switch 226 may be used to select one or more pairs for sensing cardiac electrical activity and, in particular, activity associated with the left atrium. Where a lead includes more electrodes than explicitly shown in FIG. 1, a device may include appropriate connectors to accommodate the electrodes.

Atrial sensing circuits 244 and ventricular sensing circuits 246 may also be selectively coupled to the right atrial lead 104, coronary sinus lead 106, the right ventricular lead 108 and/or the lead 110 through the switch 226 for detecting the presence of cardiac activity in each of the four chambers of the heart and/or detecting other activity (e.g., nerve activity). Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of a signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art. Such circuitry may be used for purposes of nerve sensing and/or stimulation or other tissue sensing and/or stimulation.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals and/or other signals may also be applied to inputs of an analog-to-digital (A/D) data acquisition system 252. The data acquisition system 252 is configured to acquire intracardiac electrogram signals (or other signals), convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the lead 110 through the switch 226 to sample cardiac signals (or other signals) across any configuration of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape/waveform, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AA delay, AV delay, VV delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensor 270 may be a plurality of sensors and optionally include sensors for detecting movement and minute ventilation in the patient. Sensors may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power (e.g., stored energy) to the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Figure 3:
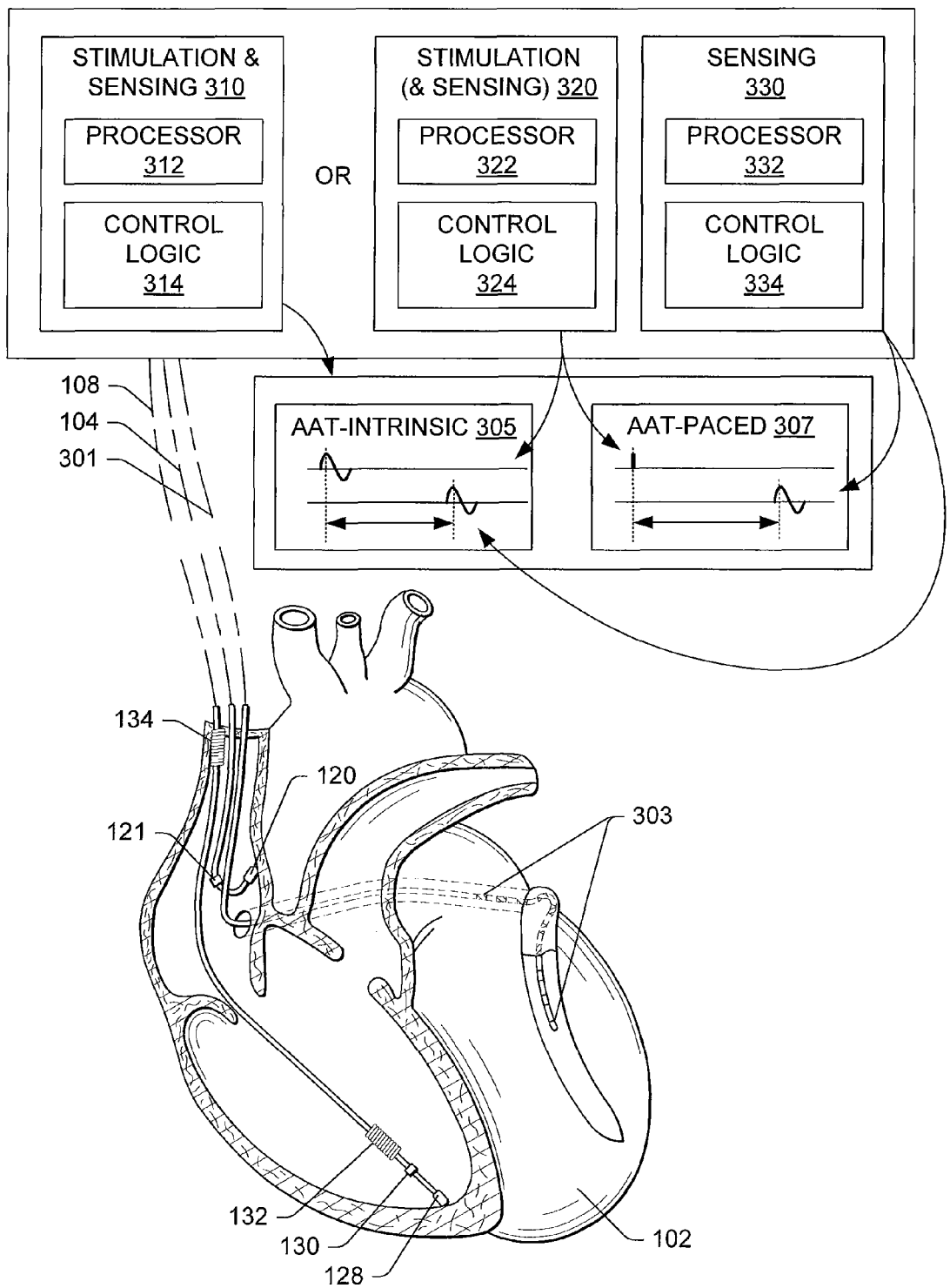
FIG. 3 is an approximate anatomical diagram of a heart and a lead with a series of electrodes for acquiring left atrial information. Various devices are also shown for acquisition of atrial information or other functions.

FIG. 3 shows an exemplary arrangement and method 300 for acquiring atrial information. Various features of the arrangement of FIG. 1 are also shown such as a right atrial lead 104 and a right ventricular lead 108. However, in this example, the arrangement includes a multi-electrode lead 301 for acquiring left atrial information. More specifically, the lead 301 includes a series of electrodes positioned in the coronary sinus and/or the great cardiac vein to sense electrical activity associated with the left atrium. The lead 301 may include features of the left ventricular lead 106 of FIG. 1 or, alternatively, the lead 106 may include features of the lead 301. Hence, an implantable lead may include features for acquiring left atrial information for use with various exemplary techniques described herein.

A plot 305 shows information associated with right atrial activity and information associated with left atrial activity. Such information may be acquired using a dedicated or a switchable sensing channel of an implantable device or using a device that operates external to the body of a patient. The plot 305 includes a time difference that corresponds to the difference between a left atrial time and a right atrial time. This time difference is referred to herein as an atrial activation time (AAT). An AAT may be considered an inter-atrial conduction delay or used to estimate an inter-atrial conduction delay. For the plot 305, both signals relate to intrinsic atrial activity such as that originating at the sinus node and hence the AAT is referred to as an intrinsic AAT (AAT-intrinsic). However, another plot 307 shows a paced atrial event for one of the atria and corresponding activity in the other atrium. Consequently, this AAT is referred to as a paced AAT (AAT-paced). Various arrows indicate how a device or devices may acquire information presented in the plots 305 and 307.

The information presented in the plots 305 and 307 may be acquired using a single stimulation and sensing device 310 or using a stimulation device 320 and a sensing device 330. The stimulation device 320 may optionally sense, as described below. The devices 310, 320 and 330 include a processor 312, 322 and 332, respectively, as well as control logic 314, 324 and 334, respectively. The control logic 314, 324 and 334 may be in the form of instructions for execution by a respective processor and/or in the form of circuitry. The control logic provides, at least, for acquisition of electrical activity and optionally determination of AAT and/or other actions.

The device 310 may be an implantable device and include various features of the device 100 of FIGS. 1 and 2. The devices 320 and 330 may be both implantable, both external or a combination thereof. In a particular example, the device 320 is an implantable device operably connected to a lead such as the lead 104 for delivery of energy to the right atrium and acquiring information associated with right atrial activity and the device 330 is an external device operably connected to a lead such as the lead 301 for acquiring information associated with left atrial activity.

Trials were performed using a right atrial lead with electrodes for delivering energy to the right atrium and acquiring information associated with right atrial activity (St. Jude Medical Corporation, Model 1688, Sylmar, California) and a decapolar lead for acquiring information associated with left atrial activity (St. Jude Medical Corporation, DAIG Model Supreme CS, Sylmar, California). The decapolar catheter had a 2-mm interelectrode distance within each pair and 5 mm of space between each electrode pair. The trials measured AAT-intrinsic and AAT-paced in fifteen patients undergoing CRT-D implantation. More specifically, the atrial lead was placed in the right atrial appendage where pacing and sensing thresholds were adequate for chronic implant while the mapping catheter was placed in coronary sinus and the great cardiac vein with the distal electrode pair positioned to measure left atrial depolarization. With the lead and catheter in position, lead pins for various electrodes were connected to an external device (EP lab system) for acquiring electrical activity (e.g., electrograms) and for delivering stimulation energy.

For these trials, AAT-intrinsic was defined using the time of onset of a P-wave (acquired using the right atrial lead) to the time of a last associated event in the distal coronary sinus (acquired using the decapolar lead) while AAT-paced was defined using the time of an atrial stimulus (delivered using the right atrial lead) to the time of a last associated event in the distal coronary sinus (acquired using the decapolar lead). AAT for sinus and paced depolarization was measured on the EP lab system and averaged over a minimum of three cardiac cycles.

The patients that participated in the trials had the following characteristics:

| | | |
|---|---|---|
| Mean age: | 68 +/− 9 years | |
| Total Patients: | 60% male | |
| Mean LVEF: | 25 + 6% | |
| CAD: | 67% | |
| Atrial arrhythmia: | AT: 8% | AF: 17% |
| NYHA Classification: | Class II: 17% | Class III: 83% |

AAT was measurable in 15 out of 15 patients where measured intrinsic AAT was 127+/−23 ms and measured paced AAT was 165+/−14 ms. All fifteen patients showed interatrial conduction delay (increased AAT) following pacing pulses from the right atrial appendage.

Figure 4:
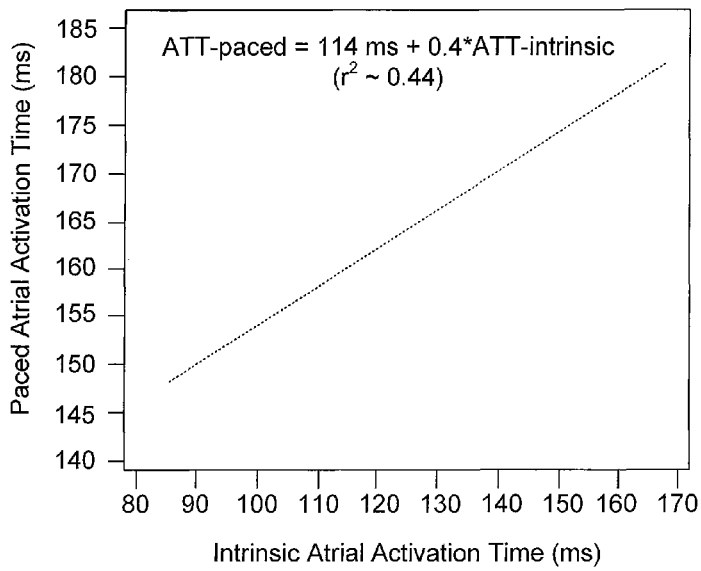
FIG. 4 is a pair of plots and a block diagram of an exemplary method for fitting a model for use in predicting paced atrial information based on intrinsic atrial information.
Figure 4:
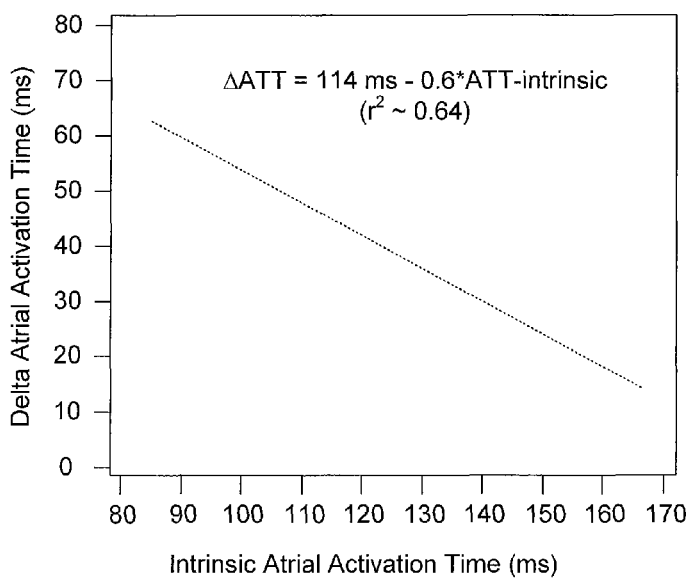
Figure 4:
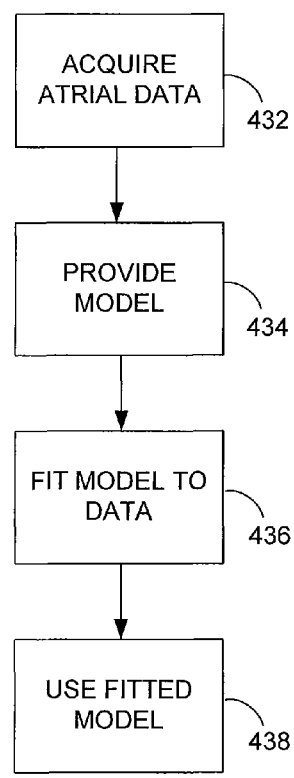

FIG. 4 shows results of a regression analysis for the patient data from the trials. In particular, a plot 410 shows a regression analysis model line for AAT-paced versus AAT-intrinsic and another plot 420 shows a difference between AAT-paced and AAT-intrinsic versus AAT-intrinsic. Plot 420 indicates that as AAT-intrinsic increases, Δ ATT decreases. The high correlation between paced and intrinsic atrial activation time suggests that the intrinsic depolarization duration is predictive of the paced duration. Hence, as described herein, the linear models applied to the data can be used for programming one or more pacing parameters. The models 410 and/or 420 may be particularly suitable for empirical programming of atrioventricular delay during atrial pacing with CRT. Models may be used in conjunction with echocardiographic information or other diagnostic information from a single patient or a patient group. While the data used in the models 410 and 420 are from a group of patients, an exemplary method may acquire information about a single patient, optionally over a range of intrinsic AATs. An exemplary method may periodically cause a device such as the device 310 to acquire an intrinsic AAT and an associated paced AAT. Such data may be analyzed for a single patient or a group of patients using a model. Of course, heart rate may have some effect on AAT-intrinsic and/or AAT-paced. Rate based scenarios are discussed further below (see, e.g., the method 800 of FIG. 8).

As described herein, various exemplary methods use AAT-intrinsic to predict AAT-paced. Where AAT-paced can be measured, verification may occur. Further, atrial rate may be adjusted or noted and AAT-paced measured to determine a relationship between a predicted AAT-paced and actual AAT-paced for various rates. Again, such information may be acquired for a single patient or for a group of patients and then used accordingly.

FIG. 4 also shows an exemplary method 430. The method commences in an acquisition block 432 that acquires right atrial activity data and left atrial activity data. A provision block 434 provides a model or models, for example, based on a prior knowledge or selected from a variety of mathematical models (e.g., linear, non-linear, etc.). A fitting or regression analysis block 436 fits the model or models to the activity data. If the fit is appropriate according to one or more criteria, then a prediction block 438 uses the model or models to predict, for example, a paced interatrial conduction delay based at least in part on an intrinsic interatrial conduction delay. Such a method may acquire data for a group of patients. Such a method may acquire right atrial data using a right atrial lead implanted in the right atrial appendage of a patient and/or left atrial data using a lead implanted at least in the coronary sinus of a patient. As already explained, a model may be a linear model and fitting may occur using a regression analysis. A model may include two or more model parameters. For example, a linear model may include a slope and an intercept.

The acquired data may be in the form of atrial activation times or may be data that requires further analysis to determine such times or equivalents thereof. As described further below, an exemplary method may include acquiring rate data and a model may include a rate variable. A regression analysis may consider the rate variable or data may be sorted based on rate and then analyzed. The exemplary method 430 may be in the form of processor-executable instructions stored on one or more computer-readable media.

Overview of Techniques for Determining Preferred A-VP Delay

Figure 5:
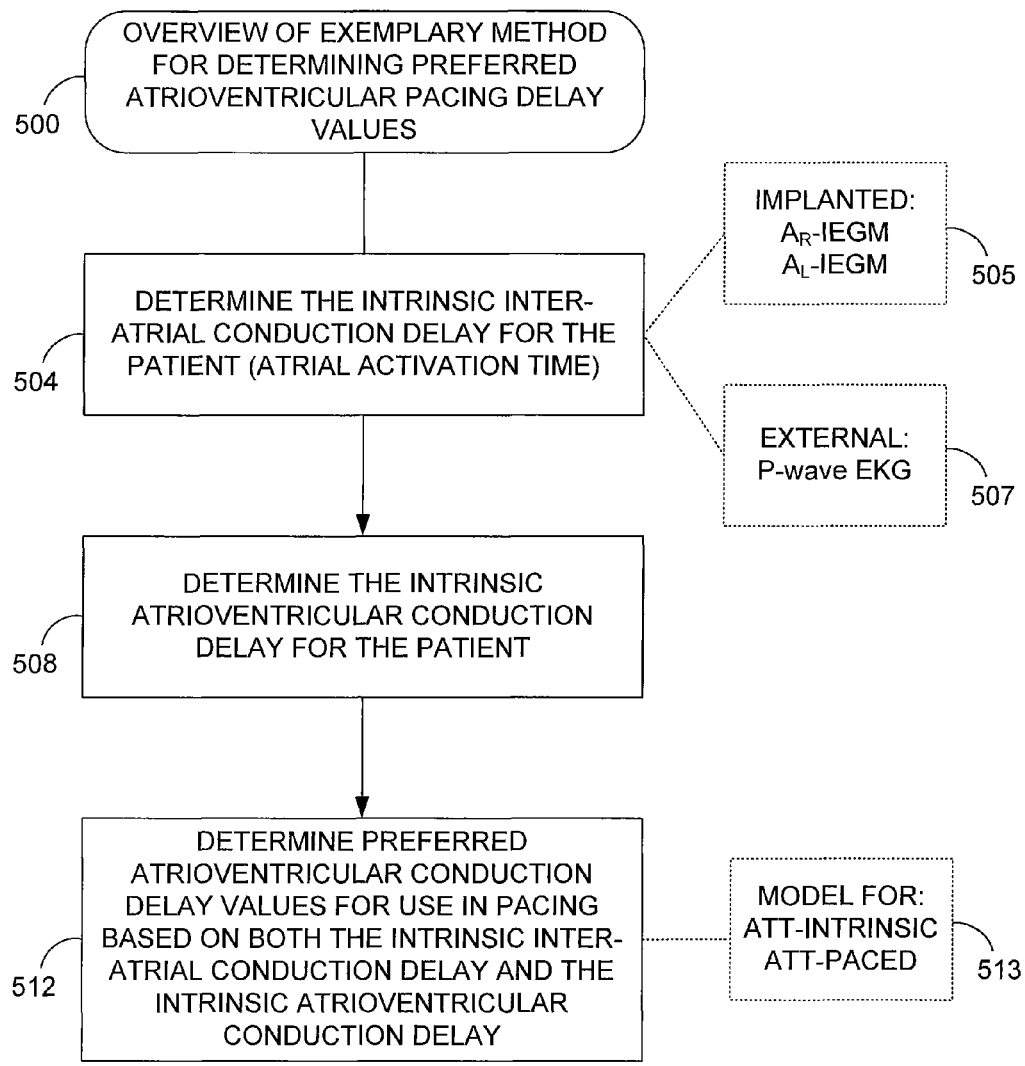
FIG. 5 is a block diagram of an exemplary method that optionally uses a predictive model to determine one or more pacing parameters.

FIG. 5 shows an overview for an exemplary method 500 for determining atrioventricular pacing delay values (A-VP). Various aspects of such a method are discussed in co-pending U.S. patent application Ser. No. 10/928,586, filed on Aug. 27, 2004, SYSTEM AND METHOD FOR DETERMINING OPTIMAL ATRIOVENTRICULAR DELAY BASED ON INTRINSIC CONDUCTION DELAYS, which is incorporated herein by reference. As described herein the various exemplary techniques of FIGS. 3 and 4 may be used, where appropriate, to determine A-VP (e.g., automatically or otherwise), to predict AAT-paced and/or to avoid premature left ventricular pacing. For example, blocks 512, 513 of FIG. 5, described below, may use a model in determining A-VP.

Within FIG. 5, a determination block 504 determines an intrinsic inter-atrial conduction delay for a patient. The intrinsic inter-atrial conduction delay represents a time delay for propagation of electrical activity (sinus node activity) from one atrium to the other via myocardial tissue. Atrial activation time (AAT), as already mentioned, refers more generally to duration of activity associated with the right atrium and activity associated with the left atrium where an AAT may be an intrinsic AAT (AAT-intrinsic) or a paced AAT (AAT-paced).

As indicated by block 505, a device may be equipped to sense both left and right atrial IEGM signals (e.g., $A_R$-IEGM and $A_L$-IEGM) using electrodes implanted in the body of a patient. For example, such a device may sense electrical activity associated with a single atrial event (e.g., a native or intrinsic atrial event or an atrial paced event) at two different sites where one site is associated the right atrium and another site is associated with the left atrium. Where two (or more) sensing sites are used, an inter-atrial conduction delay may be determined using any of a variety of techniques (e.g., time for peak amplitude in right atrium to time for peak amplitude in left atrium, time of maximum derivative in right atrium to time for maximum derivate in left atrium, etc.).

In an alternative example, as indicated by block 507, duration of electrical activity may be used (sometimes referred to as wave "width") using one or more electrodes external to the body (e.g., cutaneous or surface electrodes). For example, an atrial wave sensed using a surface EKG may be used. Such a wave is often referred to as a P-wave for intrinsic activity or an A-wave for paced activity. As discussed herein, the term P-wave may be used broadly and include the term A-wave. Thus, the term P-wave may refer to features of a surface EKG that corresponds to intrinsic atrial depolarization or paced atrial depolarization (i.e., an evoked response) that would correspondingly appear in an A-IEGM signal (i.e., acquired using one or more implanted electrodes). Typically, a surface EKG P-wave differs in form (e.g., shape and width) from its corresponding wave acquired using an A-IEGM sensing channel(s) due to electrode configuration and, in particular, proximity of an electrode or electrodes to electrical activity of the myocardium.

In yet another alternative, a combination of internal and external electrodes may be used to acquire atrial information suitable for determining an inter-atrial conduction delay. For example, a characteristic or characteristics of atrial electrical activity sensed using implanted electrodes (e.g., IEGM) may be used in combination with a characteristic or characteristics of atrial electrical activity sensed using external electrodes (e.g., EKG).

According to the method 500, a determination block 508 determines an intrinsic atrioventricular conduction delay (abbreviated AV or AV delay) for a patient. The intrinsic AV delay represents the time delay for electrical signals to be conducted from the atria to the ventricles via myocardial tissue (e.g., via the atrioventricular node and related structures). This determination may be made by detecting an atrial electrical event and a subsequent ventricular electrical event caused by the atrial electrical event. Separate intrinsic AV delay values may be determined for the left and right ventricles (e.g., $AV_{RV}$, $AV_{LV}$). Once both the intrinsic inter-atrial conduction delay and AV delay values have been determined then yet another determination block 512 determines a preferred or optimal AV delay for use in pacing (A-VP) based at least in part on the intrinsic delay values of blocks 504 and 508. By taking into account the intrinsic inter-atrial conduction delay as well as the intrinsic AV delay, preferred or optimal A-VP delay values can be reliably determined, optionally without requiring use of Doppler echocardiography and the like.

As already mentioned and as indicated by block 513, the determination block 512 may use an exemplary model (e.g., model 410 or model 420 of FIG. 4) in determining AV-P. For example, where ATT-intrinsic is available, ATT-paced may be determined using model 410 or model 420. Where atrial pacing occurs, ATT-paced may be used, for example, to determine a ventricular pacing time that avoids premature contraction of the left ventricle or, in other words, a time that allows for adequate left ventricular filling from the left atrium prior to contraction of the left ventricle.

Figure 9:
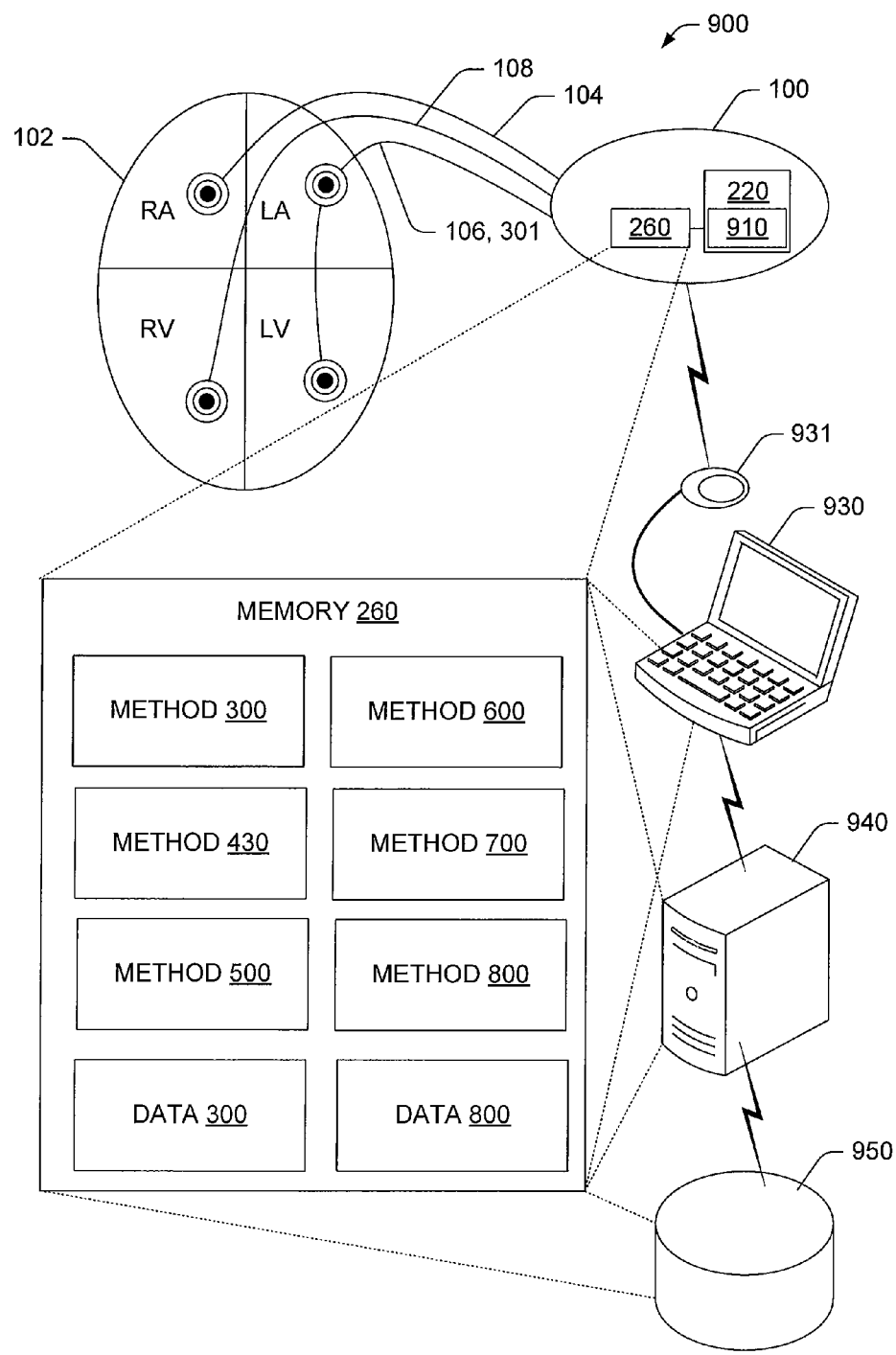
FIG. 9 is a block diagram of an exemplary system that includes an implantable device and one or more external devices and other features which may be used in implementing any of the various exemplary methods described herein.

Depending upon capabilities for sensing left and right atrial IEGM signals, the steps of FIG. 5 may be performed by an implanted device (see, e.g., FIGS. 1, 2 and 9) or may be performed in part by an implanted device and in part by an external programmer (see, e.g., FIG. 9). For implementations in which the entire determination is performed by an implanted device, the preferred or optimal A-VP delay values may be recalculated as often as needed. For example, newly sensed atrial and/or ventricular IEGM signals may be used to update an A-VP delay and thereby maintain optimal delivery of a therapy. Even in implementations where an external programmer is employed (e.g., implementations that utilize a surface EKG to aid in the determination of the intrinsic inter-atrial delay, to perform calculations, etc.), substantial benefits may be gained when compared to conventional A-VP delay optimization techniques. For example, during routine follow-up sessions between patient and physician, the optimal or preferred A-VP delay can be recalculated and reprogrammed based only upon electrical cardiac signals sensed by the implanted device in combination with a surface EKG. Where the need for Doppler echocardiography the like is eliminated or reduced, costs diminish. Further, a physician may have more time to focus on optimizing A-VP delay as opposed to setting an A-VP delay to a default or other value based on a less accurate technique (e.g., less information, dated information, poorer model, etc.). Hence, use of models such as the model 410 and the model 420 can benefit a patient by improving cardiac performance.

Figure 6:
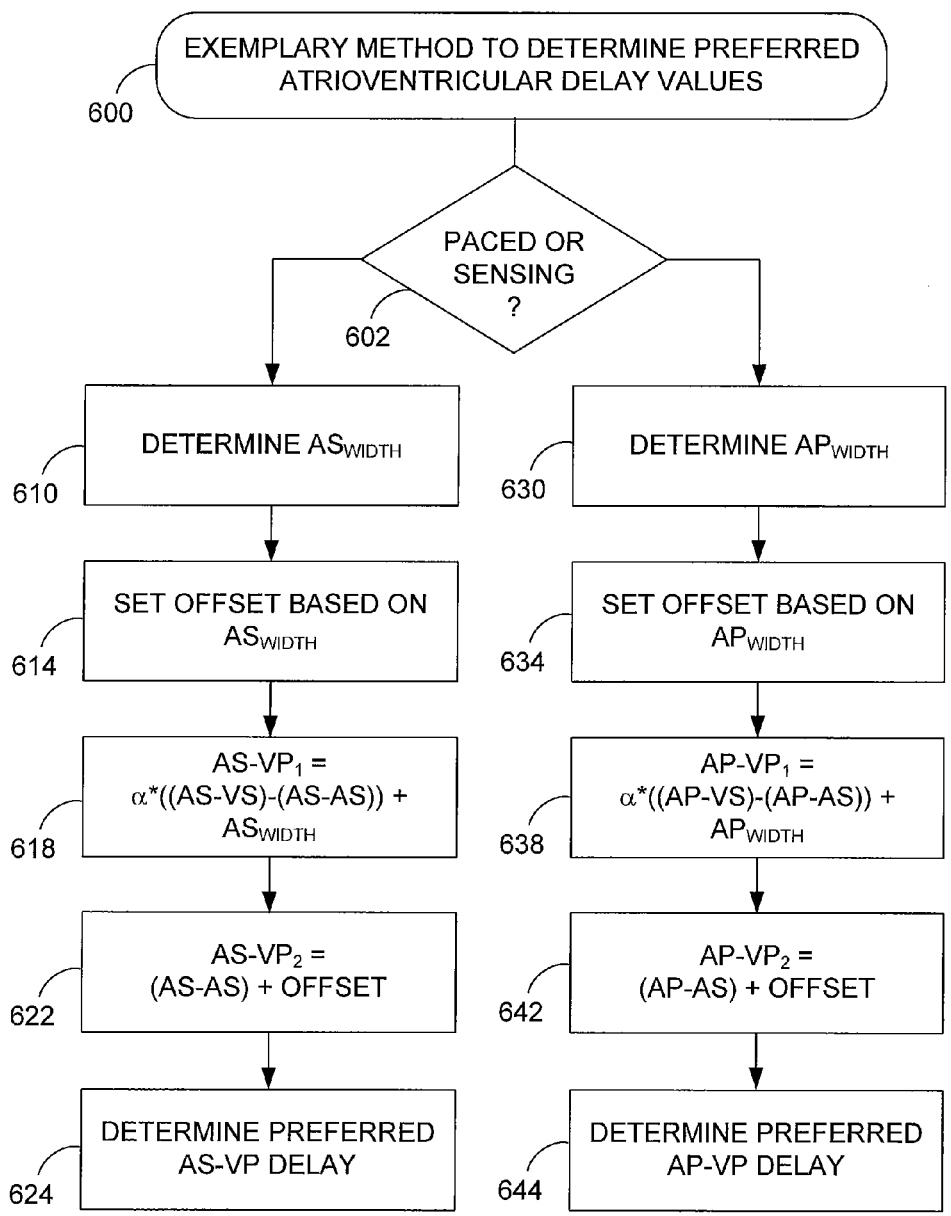
FIG. 6 is a block diagram of an exemplary method that includes a branch for intrinsic atrial activation and a branch for paced atrial activation where a model may be used to determine an atrioventricular delay (e.g., an AS-VP delay or AP-VP delay).

FIG. 6 shows an overview for an exemplary method 600 for determining AV pacing delay values (A-VP) based at least in part on width of an atrial event. For example, an atrial event width may be an intrinsic atrial event width (AS width) or a paced atrial event width (AP width). Various aspects of such a method are discussed in co-pending U.S. patent application Ser. No. 10/928,586, filed on Aug. 27, 2004, SYSTEM AND METHOD FOR DETERMINING OPTIMAL ATRIOVENTRICULAR DELAY BASED ON INTRINSIC CONDUCTION DELAYS, which is incorporated herein by reference. As described herein the various exemplary techniques of FIGS. 3 and 4 may be used, where appropriate, to determine A-VP (e.g., automatically or otherwise), to predict AAT-paced and/or to avoid premature left ventricular pacing.

According to the method 600, a decision block 602 decides if atrial pacing is used. If the decision block 602 decides atrial pacing is not used, then the method 600 proceeds along an intrinsic branch (AS branch) that includes blocks 610-624; however, if the decision block 602 decides that atrial pacing is used, then the method 600 proceeds along a paced branch (AP branch) that includes blocks 630-644.

The intrinsic branch commences with a determination block 610 to determine width of a sensed intrinsic atrial depolarization using an A-IEGM channel signal (i.e., $AS_{WIDTH}$). This width may be determined within an A-IEGM signal by identifying the beginning and end of atrial depolarization. Conventional detection techniques may be employed to detect the beginning and the end of an intrinsic atrial event. Where a value indicative of the width of an atrial depolarization is provided, then the method may use the value in lieu of determining such a value through sensing atrial activity.

The paced branch commences with a determination block 630 to determine width of an evoked response using an A-IEGM channel signal ($AP_{WIDTH}$). The width may be determined by identifying the beginning and the end of an individual evoked response or by the timing of an atrial stimulation pulse and the end of an evoked response caused by the pulse, etc.

As already explained, the models 410 and 420 of FIG. 4 may be used to determine AP information on the basis of AS information (or vice versa). Such techniques are described in further detail with respect to FIGS. 7 and 8. Thus, the AP branch or the AS branch of FIG. 6 can benefit from such models.

To calculate an optimal AS-VP, beginning at block 614, an offset value, based upon one or more $AS_{WIDTH}$ values (e.g., a single value, an average, etc.), is determined. For example, if $AS_{WIDTH}$ is greater than a predetermined width-based threshold $W_1$ (e.g. 120 ms), then the offset value is set to $T_1$ (e.g. 30 ms). If $AS_{WIDTH}$ is less than or equal to $W_1$, then the offset is instead set to $T_2$ (e.g. 60 ms.) The following equations summarize such a determination:

Offset=30 ms if $AS_{WIDTH}$>120 ms

Offset=60 ms otherwise.

The values for $W_1$, $T_1$ and $T_2$ are merely exemplary values. Routine experimentation may be performed to identify optimal values for these parameters. Referring again to the AS branch, at block 618 a first candidate AS-VP delay value based upon the intrinsic AV delay and intrinsic inter-atrial delay values already calculated for sensed events is calculated as follows:

$AS\text{-}VP_1 = \alpha*((AS\text{-}VS)-(AS\text{-}AS))+AS_{WIDTH}$.

In the foregoing equation, the coefficient α is a programmable value set to, for example, 0.5. Trials may be performed to identify an optimal value or values for α. At block 622, a second candidate AS-VP delay value is calculated, this time based upon only the intrinsic inter-atrial delay value and the aforementioned offset (i.e., in manner that does not use an AV delay):

$AS\text{-}VP_2 = AS\text{-}AS+\text{Offset}$.

At block 624, a preferred or optimal AS-VP delay is then determined by any of a variety of techniques or criteria. For example, the block 624 may include selecting the smaller of the two candidate values as follows:

$AS\text{-}VP = \text{MIN}(AS\text{-}VP_1, AS\text{-}VP_2)$.

Various trials indicate that this value represents an optimal AS-VP delay for achieving optimal cardiac performance and at the very least, a preferred AS-VP delay. In an alternative, a device may be programmed to select either the first candidate value or the second candidate value, to average the values together, etc. Once implemented, feedback may occur via sensed information, via the patient, etc., and a change may occur from the first to second or vice versa. In another scenario, the various values may be presented to the physician who is then prompted to select one of the candidate values.

Thus, steps 610-624 operate to determine a preferred or optimal AS-VP delay value. Where this value is determined using an external device, the value (or values) may be transmitted to an implanted device, which uses the value to time delivery of ventricular pacing pulses following intrinsic atrial events in accordance with otherwise conventional techniques.

Similar steps are performed along the paced branch to identify an optimal or preferred AP-VP delay value. Briefly, at block 634, an offset value is determined, this time based upon one or more $AP_{WIDTH}$ values (e.g., a single value, an average, etc.) and a different threshold value. As already mentioned, FIGS. 7 and 8 describe techniques to determine AP information on the basis of AS information and vice versa. Such techniques may be used in determining an offset value.

According to an exemplary scenario, if $AP_{WIDTH}$ is greater than a predetermined width-based threshold $W_2$ (e.g. 100 ms), then the offset value is set to $T_1$ (e.g., 30 ms). If $AP_{WIDTH}$ is less than or equal to $W_2$, then the offset is instead set to $T_2$ (e.g., 60 ms). The following equations summarize such a determination:

Offset=30 ms if $AP_{WIDTH}$>100 ms

Offset=60 ms otherwise.

The values for $W_2$, $T_1$ and $T_2$ are merely exemplary values. Trials may be performed to identify optimal values for these parameters. Then, at blocks 638 and 642, a pair of candidate AP-VP delay values is derived using the following equations:

$AP\text{-}VP_1 = \alpha*((AP\text{-}VS)-(AP\text{-}AS))+AP_{WIDTH}$ $AP\text{-}VP_2 = AP\text{-}AS+\text{Offset}$.

The coefficient α may be same as used above for AS-VP (i.e., 0.5), or it may differ. Trials may be performed to identify an optimal value of α. Finally, at block 644, a single preferred AP-VP delay value is selected, for example, from the pair candidate values as follows:

$AP\text{-}VP = \text{MIN}(AP\text{-}VP_1, AP\text{-}VP_2)$.

Various trials indicate that this value represents an optimal AP-VP delay for achieving optimal cardiac performance and at the very least, a preferred AP-VP delay. In an alternative, a device may be programmed to select either the first candidate value or the second candidate value, to average the values together, etc. Once implemented, feedback may occur via sensed information, via the patient, etc., and a change may occur from the first to second or vice versa. In another scenario, the various values may be presented to the physician who is then prompted to select one of the candidate values.

An exemplary method includes providing an intrinsic atrial waveform width (e.g., $AS_{WIDTH}$), determining a paced atrial waveform width ($AP_{WIDTH}$) using a predictive model and the intrinsic atrial waveform width, determining an atrioventricular delay (e.g., AP-VP) based at least in part on the paced atrial waveform width and programming an implantable device to deliver a therapy using the atrioventricular delay wherein the therapy uses atrial pacing and ventricular pacing. Such a method may include determining an atrioventricular delay using an offset based on the paced atrial waveform width. As indicated in block 642, such a method may determine an atrioventricular delay by adding an offset and a paced interatrial conduction delay. As described further below, an exemplary method may adjust an atrioventricular delay with respect to a pacing rate. For example, such adjusting may multiply an atrioventricular delay by a ratio of a pacing rate to a specified rate. As already mentioned, a predictive model may be a linear model, a non-linear model, a look-up table, etc. A model may include one or more parameters determined using a regression analysis of data acquired from a group of patients or a single patient. A determined atrioventricular delay (e.g., AP-VP) may avoid premature left ventricular activation (i.e., by allowing for adequate LV filling). Various exemplary methods may be in the form of processor-executable instructions stored on one or more computer-readable media.

While the foregoing exemplary method refers to atrial activity width such as $AS_{WIDTH}$ and $AP_{WIDTH}$, an exemplary method may use AAT-intrinsic and AAT-paced with or without resorting to use of $AS_{WIDTH}$ and $AP_{WIDTH}$. An exemplary method includes providing an intrinsic atrial activation time, determining a paced atrial activation time using a predictive model and the intrinsic atrial activation time, determining an atrioventricular delay based at least in part on the paced atrial activation time and programming an implantable device to deliver a therapy using the atrioventricular delay wherein the therapy uses atrial pacing and ventricular pacing. In such a method, a relationship may exist for determining an offset or offsets based on AAT. In turn, such an offset or offsets may be used to determine one or more AP-VP values. A determined atrioventricular delay (e.g., AP-VP) may avoid premature left ventricular activation (i.e., by allowing for adequate LV filling).

Figure 7:
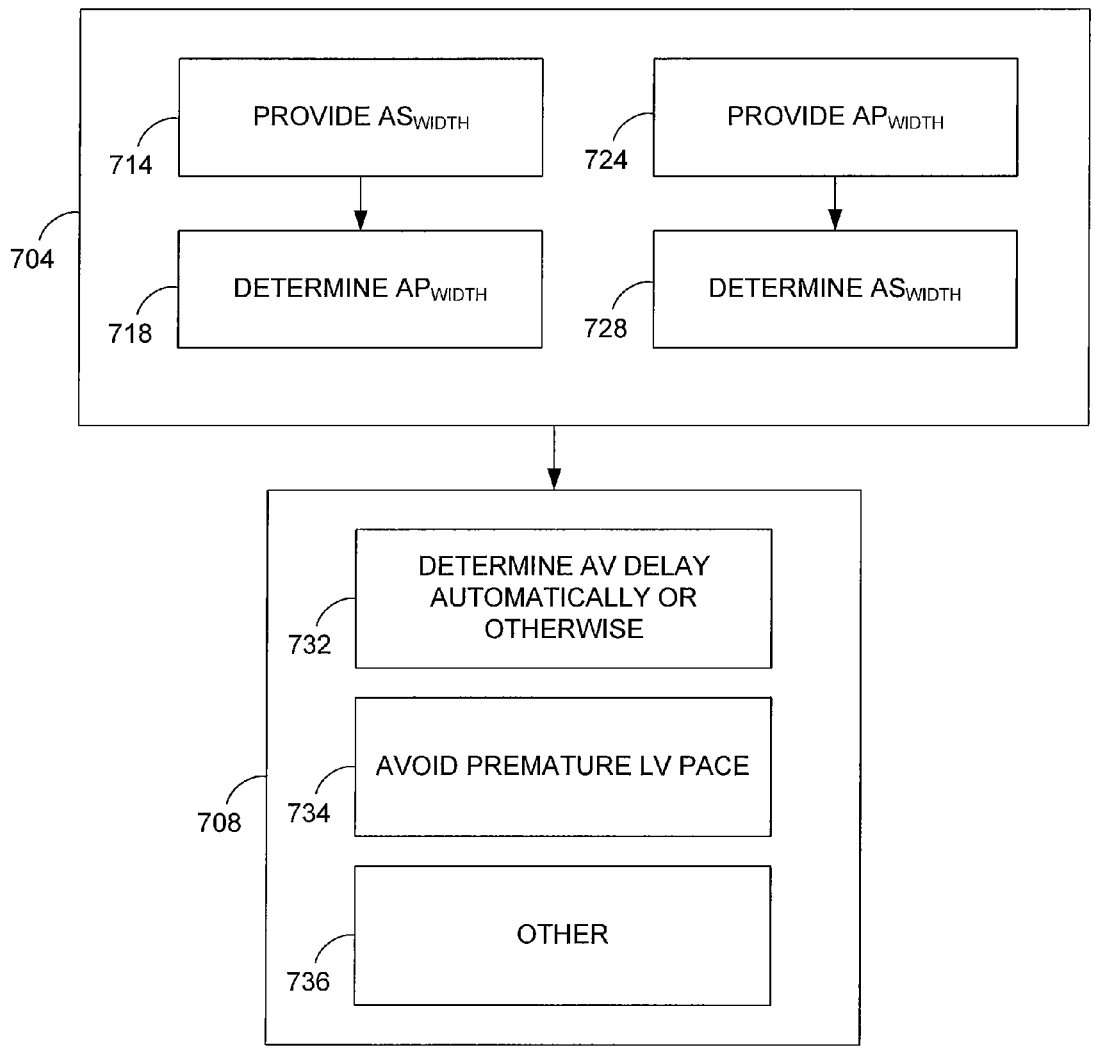
FIG. 7 is a block diagram of an exemplary method that uses a predictive model for any of a variety of purposes related to cardiac therapy.

FIG. 7 shows an exemplary method 700 for determining $AP_{WIDTH}$ using $AS_{WIDTH}$ or vice versa. For example, the model 410 or the model 420 may be used to determine or otherwise estimate $AP_{WIDTH}$ given $AS_{WIDTH}$. Such models may be rearranged mathematically to determine or estimate $AS_{WIDTH}$ given $AP_{WIDTH}$. The method 700 includes a determination block 704 that includes an AS to AP branch and an AP to AS branch. More specifically, for the AS to AP branch, a block 714 provides an $AS_{WIDTH}$ and a determination block 718 determines an $AP_{WIDTH}$ based on the $AS_{WIDTH}$ and patient data, a model, a look-up table, etc., where the determination relies on a relationship between intrinsic atrial activity and paced atrial activity (see, e.g., the relationships of FIG. 4).

For the AP to AS branch, a block 724 provides an $AP_{WIDTH}$ and a determination block 728 determines an $AS_{WIDTH}$ based on the $AP_{WIDTH}$ and patient data, a model, a look-up table, etc., where the determination relies on a relationship between intrinsic atrial activity and paced atrial activity (see, e.g., the relationships of FIG. 4).

The method 700 further includes an implementation block 708 that implements a pacing therapy or other therapy based at least in part on a determination of the determination block 704. For example, a block 732 determines A-VP delay automatically or otherwise based at least in part on $AP_{WIDTH}$ or $AS_{WIDTH}$ of the blocks 718 or 728, respectively; an aversion block 734 avoids premature LV pacing based at least in part on $AP_{WIDTH}$ or $AS_{WIDTH}$ of the blocks 718 or 728, respectively; and an other action block 736 calls for other action or actions germane to a patient therapy (e.g., a cardiac pacing therapy) based at least in part on $AP_{WIDTH}$ or $AS_{WIDTH}$ of the blocks 718 or 728, respectively.

Figure 8:
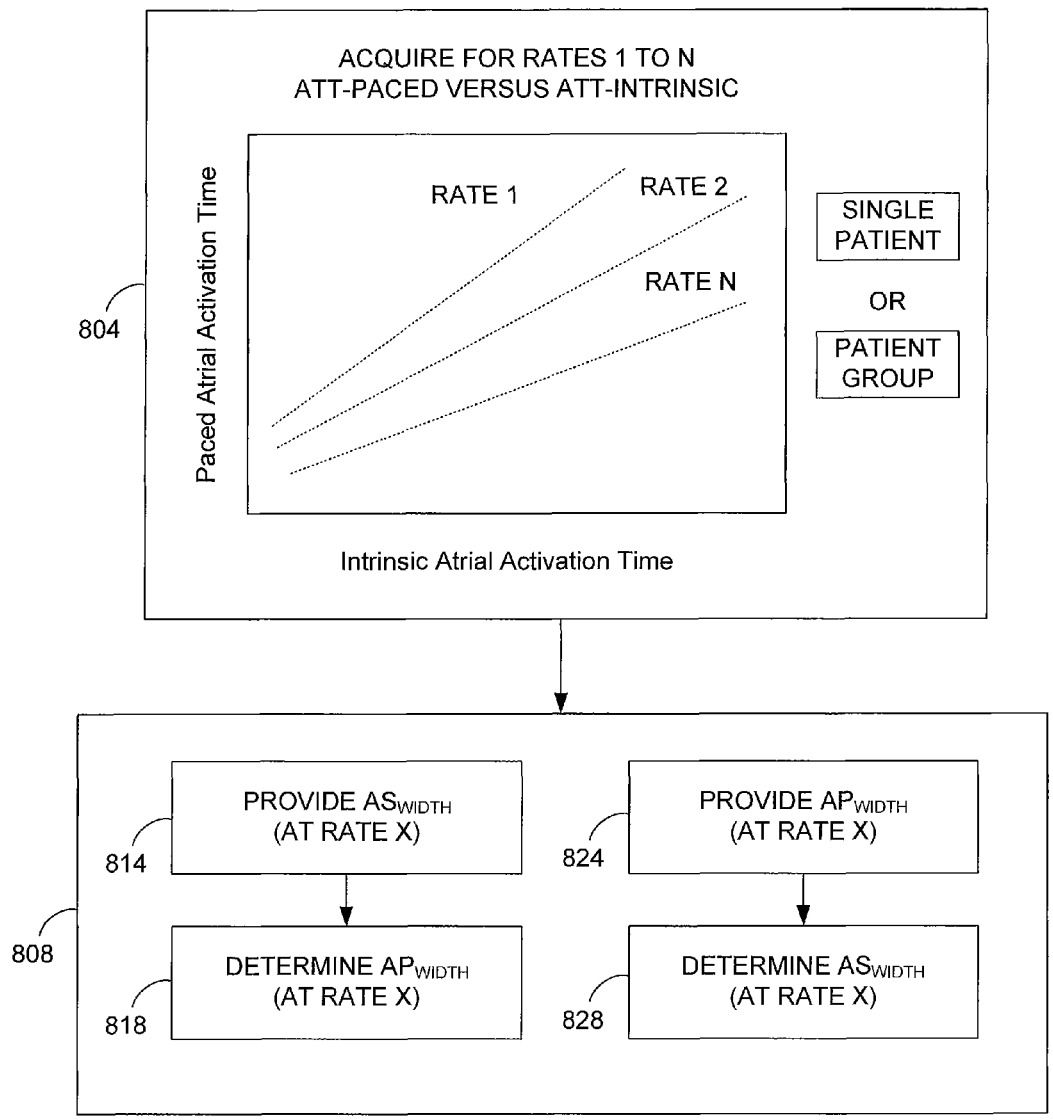
FIG. 8 is a plot of atrial information based at least in part atrial rate and a block diagram of an exemplary method for using such information.

FIG. 8 shows exemplary data and an associated exemplary method 800. A plot 804 shows data or models as AAT-paced versus AAT-intrinsic for various rates (e.g., Rate 1, Rate 2, . . . , Rate N). Such data may be acquired from a single patient or from a group of patients. For example, data may be pooled for a single patient and/or from a variety of patients and then analyzed based on rate. Exemplary data may include substantially contemporaneous AAT-intrinsic, AAT-paced, rate information (e.g., intrinsic and/or paced rate information). While separate lines are shown, an analysis may create a surface in two or three dimension to aid in determining one or more therapy parameters.

A determination block 808 includes an AS to AP branch and an AP to AS branch. More specifically, for the AS to AP branch, a block 814 provides an $AS_{WIDTH}$ for a particular rate and a determination block 818 determines an $AP_{WIDTH}$ for that rate based on the $AS_{WIDTH}$, the rate and patient data, a model, a look-up table, etc., where the determination relies on a relationship between intrinsic atrial activity and paced atrial activity.

For the AP to AS branch, a block 824 provides an $AP_{WIDTH}$ for a particular rate and a determination block 828 determines an $AS_{WIDTH}$ based on the $AP_{WIDTH}$, the rate and patient data, a model, a look-up table, etc., where the determination relies on a relationship between intrinsic atrial activity and paced atrial activity. For either branch, determined value may be used accordingly, for example, per the blocks 732, 734, 736 of FIG. 7.

Other rate adjustments are possible as well and may be used alternatively or in addition to an exemplary technique such as that of FIG. 8. More specifically, as already mentioned, various trials indicate that an optimal A-VP delay (e.g., AS-VP or AP-VP) for achieving optimal cardiac performance occurs for a specified pacing rate (e.g., base rate) and, at the very least, represents a preferred A-VP delay for a specified pacing rate (e.g., base rate).

For pacing rates that are not at a specified rate, for example, a base rate or for intrinsic rates that are not at a rest rate, optimal AP-VP and AS-VP delay values may be automatically or otherwise adjusted by an implantable device and/or an external programmer. For example, for sensed events the AS-VP pacing delay value may be adjusted as follows:

Rate Adjusted $AS\text{-}VP = \alpha^* (AS\text{-}VP)$ where α=current heart rate/rest rate (or other specified rate).

For paced events in atria, the AP-VP value may be adjusted as follows:

Rate Adjusted $AP\text{-}VP = \alpha^* (AP\text{-}VP)$ where α=current pacing rate/base rate (or other specified rate).

FIG. 9 shows an exemplary system 900 that includes the exemplary implantable device 100 of FIGS. 1 and 2, with processor 220 including one or more modules 910, for example, that may be loaded via memory 260. A series of leads 104, 106 and 108 (and/or lead 301) provide for delivery of stimulation energy and/or sensing of cardiac activity, etc., associated with the heart 102. Stylized bullets indicate approximate positions or functionality associated with each of the leads 104, 106 and 108 (and/or lead 301). Other arrangements are possible as well as use of other types of sensors, electrodes, etc.

Memory 260 is shown as including modules (e.g., processor-executable instructions) for performing various actions of the methods 300-800, noting that part of a method may be performed using a device other than the implantable device 100. Memory 260 may also include data 300 and 800, optionally for use by the device 100 and/or an external device.

The system 900 includes a device programmer 930 having a telemetry unit 931 for communicating with the implantable device 100. The programmer 930 may further include communication circuitry for communication with another computing device 940, which may be a server. The computing device 940 may be configured to access one or more data stores 950, for example, such as a database of information germane to a patient, an implantable device, therapies, etc. Such a data store may include information for patients such as the AAT information of FIG. 4 or 8.

An exemplary device includes a power source, a processor, memory and control logic to determine a paced atrial activation time using a predictive model and an intrinsic atrial activation time and to determine an atrioventricular delay based at least in part on the paced atrial activation time. Such a device may be an implantable device or a computing device that may communicate the atrioventricular delay to an implantable device. For example, the device 930 may program the device 100 with an atrioventricular delay for use in a therapy that uses atrial pacing and ventricular pacing.

Various empirically-derived exemplary models may be used to predict a difference in atrial activation time and intrinsic atrial depolarizations and paced atrial depolarizations (e.g., paced interatrial conduction delay). As explained with respect to FIG. 4, observations of measured paced and native beats show a high degree of correlation such that an empirically derived formula may be determined for use by a pacemaker, ICD, CRT device, or a programmer for prediction of a patient's interatrial conduction delay thus providing appropriate information for programming of atrioventricular delays. For example, by providing a measurement of the intrinsic atrial activation time, a paced atrial activation time may be calculated or otherwise determined (e.g., look-up table). Such a difference in atrial sensed and paced atrial activation times may be added to a sensed AV delay to allow sufficient time for passive and active filling of the left ventricle.

CONCLUSION

Although exemplary methods, devices and/or systems have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices and/or systems.

What is claimed is:

1. A method of using an implantable device comprising:
acquiring right atrial activity data and left atrial activity data for intrinsic atrial activations and paced atrial activations, the data sufficient to determine intrinsic atrial activation times and paced atrial activation times;
providing a model for paced atrial activation times as a function of intrinsic atrial activation times;
fitting the model to the data;
using the model to predict a paced atrial activation time based on a subsequently determined intrinsic atrial activation time; and using the predicted paced atrial activation time to provide pacing to an atria.

2. The method of claim 1 wherein the acquiring acquires data for a group of patients.

3. The method of claim 1 wherein the acquiring right atrial data comprises using a right atrial lead implanted in the right atrial appendage of a patient.

4. The method of claim 1 wherein the acquiring left atrial data comprises using a lead implanted at least in the coronary sinus of a patient.

5. The method of claim 1 wherein the model comprises a linear model.

6. The method of claim 1 wherein the fitting comprises a regression analysis.

7. The method of claim 1 wherein the model comprises two or more model parameters.

8. The method of claim 1 wherein the acquiring comprises acquiring rate data.

9. The method of claim 1 wherein each of atrial activation times is determined as a difference between right atrial activity data corresponding to P wave onset and left atrial activity data corresponding to a last associated event in the left atria.

10. The method of claim 1 further comprising providing a model for a difference between paced atrial activation times and intrinsic atrial activation times as a function of intrinsic atrial activation times; and fitting the model to the data.

11. The method of claim 10 wherein the model represents the difference, defined as paced atrial activation times minus intrinsic atrial activation times, as decreasing with increasing intrinsic atrial activation times.

12. A method of using an implantable device comprising:
providing a predictive model for paced atrial waveform width as a function of intrinsic atrial waveform width, the predictive model fit to data corresponding to previously determined intrinsic atrial waveform widths and paced atrial waveform widths;
providing a subsequent intrinsic atrial waveform width;
predicting a paced atrial waveform width using the predictive model and the intrinsic atrial waveform width;
determining an atrioventricular delay based at least in part on the predicted paced atrial waveform width; and
programming an implantable device to deliver a therapy using the atrioventricular delay wherein the therapy uses atrial pacing and ventricular pacing.

13. The method of claim 12 wherein the determining an atrioventricular delay comprises determining an offset based on the paced atrial waveform width.

14. The method of claim 12 wherein the determining an atrioventricular delay comprises determining a paced interatrial conduction delay.

15. The method of claim 12 further comprising adjusting the atrioventricular delay with respect to a pacing rate.

16. The method of claim 12 wherein the predictive model comprises a linear model.

17. The method of claim 12 wherein the model comprises one or more parameters determined using a regression analysis of data acquired from a group of patients.

18. The method of claim 12 wherein the model comprises one or more parameters determined using a regression analysis of data acquired from a patient.

19. The method of claim 12 wherein the atrioventricular delay provides for adequate left ventricular filling based on the paced atrial waveform width.

20. The method of claim 12 wherein the determining an atrioventricular delay based at least in part on the paced atrial waveform width determines a ventricular pacing time that avoids premature contraction of the left ventricle.

21. The method of claim 12 wherein each of the intrinsic atrial waveform widths comprises a difference between a time based on right atrial activity and a time based on the left atrial activity and wherein each of the paced atrial waveform widths comprises a difference between a time of an atrial stimulus, or a time based on the right atrial activity, and a time based on the left atrial activity.

22. An implantable device comprising:
   a pulse generator configured to provide pacing pulses to an atria so as to induce paced atrial activations;
   sensing circuitry configured to sense intrinsic atrial activations and paced atrial activations; and
   a processor configured to:
      acquire right atrial activity data and left atrial activity data for intrinsic atrial activations and paced atrial activations,
      determine intrinsic atrial activation times and paced atrial activation times from the data;
      provide a model for paced atrial activation times as a function of intrinsic atrial activation times;
      fit the model to the data; and
      use the model to predict a paced atrial activation time based on a subsequently determined intrinsic atrial activation time.

* * * * *